(12) United States Patent
Chen et al.

(10) Patent No.: US 9,371,238 B2
(45) Date of Patent: Jun. 21, 2016

(54) TITANIUM-SILICALITE MOLECULAR SIEVE, METHOD FOR PREPARING THE SAME AND METHOD FOR PREPARING CYCLOHEXANONE OXIME USING THE MOLECULAR SIEVE

(75) Inventors: Ya-Ping Chen, Taipei (TW); Cheng-Fa Hsieh, Taipei (TW); Pin-To Yao, Taipei (TW); Chien-Chang Chiang, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 1204 days.

(21) Appl. No.: 13/345,089

(22) Filed: Jan. 6, 2012

(65) Prior Publication Data

US 2012/0277468 A1 Nov. 1, 2012

(30) Foreign Application Priority Data

Apr. 27, 2011 (TW) ............... 100114599 A

(51) Int. Cl.
*C01B 37/00* (2006.01)
*C01B 39/08* (2006.01)
*C07C 249/04* (2006.01)
*B01J 29/89* (2006.01)

(52) U.S. Cl.
CPC ............... *C01B 37/005* (2013.01); *B01J 29/89* (2013.01); *C01B 39/085* (2013.01); *C01B 39/087* (2013.01); *C07C 249/04* (2013.01)

(58) Field of Classification Search
CPC .. C01B 39/085; C01B 39/087; C01B 37/005; C01B 37/087
See application file for complete search history.

(56) References Cited

U.S. PATENT DOCUMENTS

| 4,968,842 A | 11/1990 | Padovan et al. |
| 5,227,525 A | 7/1993 | Tonti et al. |
| 5,290,533 A | 3/1994 | Bellussi et al. |
| 5,312,987 A | 5/1994 | Mantegazza et al. |
| 6,828,459 B2 | 12/2004 | Oikawa et al. |
| 2012/0277468 A1* | 11/2012 | Chen ............ C01B 37/005 564/267 |

FOREIGN PATENT DOCUMENTS

EP 226258 A2 6/1987

* cited by examiner

*Primary Examiner* — David M Brunsman
(74) *Attorney, Agent, or Firm* — Mintz Levin Cohn Ferris Glovsky and Popeo, P.C.; Peter F. Corless; Richard B. Emmons

(57) ABSTRACT

The present invention provides a titanium-silicalite molecular sieve and a method for preparing the same. The method includes the steps of preparing a mixture of a titanium source, a silicon source, a transition metal source, a template agent and water; heating the mixture to form a gel mixture; heating the gel mixture in a water bath; and calcining the gel mixture after the gel mixture in the water bath to form the titanium-silicalite molecular sieve. The present invention further provides a method for preparing cyclohexanone oxime by using the titanium-silicalite molecular sieve as the catalyst which results in high conversion rate, high selectivity and high usage efficiency of hydrogen peroxide.

14 Claims, 1 Drawing Sheet

Angle

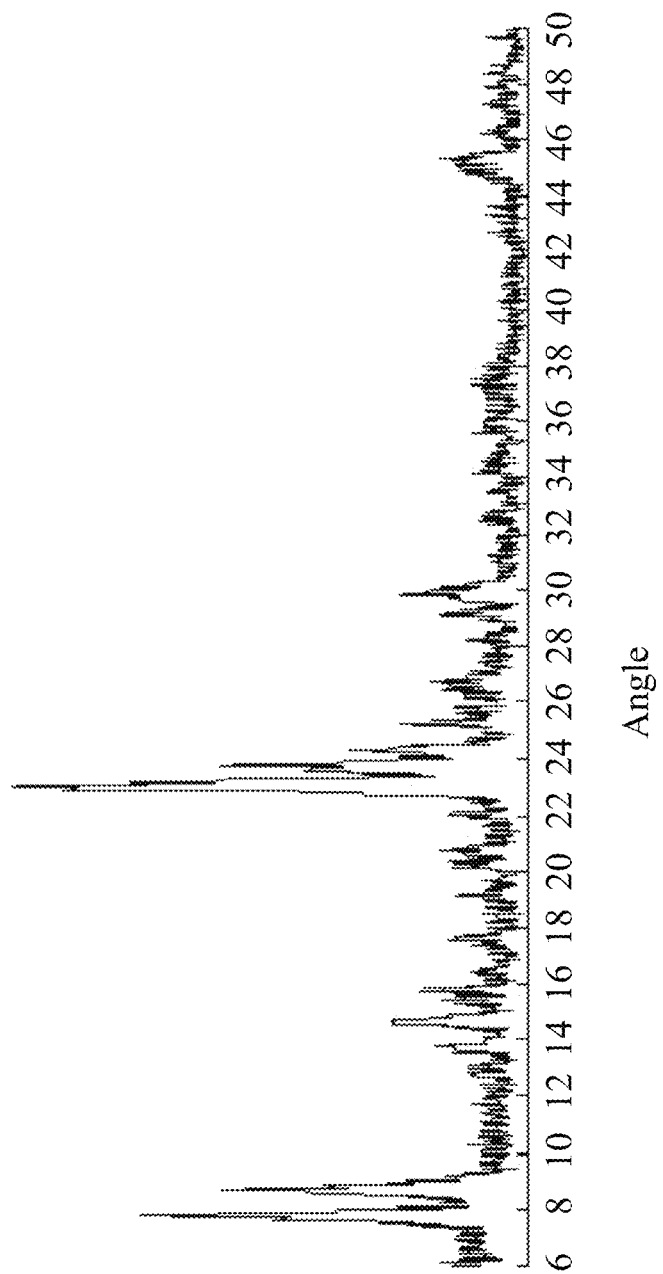

TITANIUM-SILICALITE MOLECULAR SIEVE, METHOD FOR PREPARING THE SAME AND METHOD FOR PREPARING CYCLOHEXANONE OXIME USING THE MOLECULAR SIEVE

CROSS-REFERENCES TO RELATED APPLICATIONS

This application claims under 35 U.S.C. §119(a) the benefit of Taiwanese Application No. 100114599, filed Apr. 27, 2011, the entire contents of which is incorporated herein by reference.

BACKGROUND OF THE INVENTION

1. Field of the Invention

The present invention relates to a titanium-silicalite molecular sieve and a method for preparing the same, and more particular to, a titanium-silicalite molecular sieve having a transition metal and a method for preparing the same.

2. Description of the Prior Art

Crystalline titanium-silicalite molecular sieves are formed by incorporating titanium into the zeolite structure of silicon dioxide. TS-1 molecular sieves have the MFI structures, and TS-2 molecular sieves have the MEL structures. These molecular sieves are used in oxidation reactions such as ammoximation of cyclohexanone and hydroxylation of phenol which use hydrogen peroxide as the oxidant.

Cyclohexanone oxime is the intermediate of the preparation of amides. U.S. Pat. Nos. 4,968,842, 522,752, 5,312,987 and 6,828,459 disclose using cyclohexanone, ammonia and hydrogen peroxide to form cyclohexanone oxime. However, in such methods, the use efficiency of hydrogen peroxide is about 89% to 90%. The use efficiency of hydrogen peroxide cannot be improved for lowering the production cost.

U.S. Pat. No. 5,290,533 and EP226258 disclose a method for preparing a titanium-silicalite molecular sieve having a transition metal, wherein the iron source is treated with ammonia to form the hydroxide precipitation, the hydroxide precipitation is washed, neutralized, dissolved in the template agent, mixed with the titanium-silicon solution, and then heated to form the molecular sieve. Such method is complicated.

Hence, the present invention provides a method for simplifying the preparation of the molecular sieve and a method using the molecular sieve of the invention for preparing cyclohexanone oxime which enhances the ammoximation of cyclohexanone and improves the usage efficiency of hydrogen peroxide.

SUMMARY OF THE INVENTION

The present invention provides a method for preparing a titanium-silicalite molecular sieve. The method includes the steps of preparing a mixture of a titanium source, a silicon source, a transition metal source, a template agent and water; heating the mixture to form a gel mixture; heating the gel mixture in a water bath; and calcining the gel mixture after the gel mixture in the water bath to form the titanium-silicalite molecular sieve.

In the present invention, a mole ratio of the template agent to the silicon source is less than or equal to 0.5. The transition metal source is selected from the group consisting of an acidic metal salt, a metal alkoxide and a metal complex. Preferably, the transition metal source is dissolved in the water and mixed in an aqueous form with the titanium source, the silicon source and the template agent to form the gel mixture. For example, the transition metal source may be dissolved in the water including ammonia.

Further, in the method for preparing a titanium-silicalite molecular sieve, after forming the gel mixture, the gel mixture is mixed with water or colloidal silica; and the gel mixture mixed with the water or the colloidal silica is heated in the water bath.

Generally, the colloidal silica is silicon dioxide gel solution, and an amount of the silicon dioxide is 0.1 to 50 wt % of the colloidal silica. The weight ratio of the colloidal silica to the gel mixture ranges from 0.001:1 to 0.5:1.

In addition, the present invention further provides titanium-silicalite molecular sieve, including a silicon oxide; a titanium oxide; and a transition metal oxide, wherein a molar ratio of titanium to silicon ranges from 0.005 to 0.1; and a molar ratio of a transition metal of the transition metal oxide to the silicon ranges from 0.00001 to 0.05.

Moreover, the present invention provides a method for preparing cyclohexanone oxime. The method includes the step of performing a reaction of cyclohexanone, ammonia and hydrogen peroxide in the presence of a titanium-silicalite molecular sieve of the present invention as a catalyst and a solvent.

Hence, in the method of the present invention, the transition metal source is mixed with the titanium source, silicon source and the template agent before the gem mixture is formed, such that the titanium-silicalite molecular sieve of the present invention has the transition metal oxide. The method for preparing cyclohexanone oxime by using the titanium-silicalite molecular sieve of the present invention results in high conversion rate, high selectivity, and high usage efficiency of hydrogen peroxide.

BRIEF DESCRIPTION OF THE DRAWINGS

FIG. 1 shows the X-ray spectrum of the catalyst prepared from Embodiment 2 of the present invention.

DETAILED DESCRIPTION OF THE INVENTION

The following specific embodiments are provided to illustrate the disclosure of the present invention. These and other advantages and effects can be easily understood by those skilled in the art after reading the disclosure of this specification.

The present invention provides a method for preparing a titanium-silicalite molecular sieve. The method includes the steps of preparing a mixture of a titanium source, a silicon source, a transition metal source, a template agent and water; heating the mixture to form a gel mixture; heating the gel mixture in a water bath; and calcining the gel mixture after the gel mixture in the water bath to form the titanium-silicalite molecular sieve.

Generally, the silicon source is mixed with the template agent, and then added in sequence with the titanium source and the transition metal source solution. In the present invention, the titanium source may be a tetraalkyl titanate such as tetraethyl titanate, tetraisopropyl titanate or tetrabutyl titanate. The silicon source is tetraalkyl silicate or polyethoxysiloxane such as tetramethyl silicate, tetraethyl silicate, tetrapropyl silicate or tetrabutyl silicate. The polyethoxysiloxane may be ES-28 (n=1-2), ES-32 (n=3-4) or ES-40 (n=4-5) (Colcoat CO.) In the present invention, the titanium source and the silicon source may not be limited to the above examples, and may be one or a combination of the above examples.

In the present invention, the template agent includes tetrapropylammonium hydroxide in an alcohol solvent or an aqueous solution. For example, the tetrapropylammonium hydroxide is dissolved in an alcohol or water for the anion exchange resin process. The alcohol has 1 to 5 carbons such as methanol, ethanol, isopropanol, n-butanol or tert-butanol. The concentration of the template agent may be 5 wt % to 50 wt % and preferably 20 wt % to 40 wt %. The mole ratio of the template agent to the silicon is less than or equal to 0.5.

The transition metal is selected from the group consisting of an acidic metal salt, a metal alkoxide and a metal complex. The transition metal source is dissolved in the water and mixed in an aqueous form with the titanium source, the silicon source and the template agent to form the gel mixture. The transition metal may be one or more selected from IB to VIIIB elements such as V, Fe, Co, Ni, Zn, Y, Zr, Ru, Pd and Hf.

In the mixture of the titanium source, the silicon source, the transition metal source, the template agent and water, the molar ratio of the titanium to the silicon ranges from 0.005 to 0.1, preferably 0.015 to 0.08 and more preferably 0.02 to 0.05; the molar ratio of the transition metal to the silicon ranges from 0.00001 to 0.05, preferably 0.0003 to 0.03, and more preferably 0.0005 to 0.02; the molar ratio of the water to the silicon ranges from 10 to 80, preferably 20 to 60, and more preferably 30 to 50; and the molar ratio of the template agent to the silicon ranges from 0.1 to 0.5, preferably 0.15 to 0.45, and more preferably 0.2 to 0.4.

In the present invention, after the gel mixture is formed, the gel mixture is mixed with water or colloidal silica; and the gel mixture mixed with the water or the colloidal silica is heated in the water bath. Generally, the gel mixture is mixed with silicon dioxide gel solution, and the amount of the silicon dioxide is 0.1 to 50 wt % of the colloidal silica. The silicon dioxide gel solution may be Ludox AS-40, Ludox AS-30, Ludox TM-40, Ludox TM-50, Ludox AM-30, Ludox HS-30, Ludox HS-40 (DuPont) or SNOWTEX-40, SNOWTEX-50, SNOWTEX-C, SNOWTEX-N, SNOWTEX-20L, SNOWTEX-ZL, SNOWTEX-UP (Nissan Chemical Industries, Ltd.) Further, the weight ratio of the colloidal silica to the gel mixture ranges from 0.001:1 to 0.5:1.

In the present invention, the titanium-silicalite molecular sieve includes a silicon oxide, a titanium oxide, and a transition metal oxide, wherein the molar ratio of the titanium to the silicon ranges from 0.005 to 0.1; and the molar ratio of the transition metal of the transition metal oxide to the silicon ranges from 0.00001 to 0.05. The transition metal atom of the transition metal oxide is positioned inside or outside the skeleton of the molecular sieve.

The present invention further provides a method for preparing cyclohexanone oxime. In this method, the titanium-silicalite molecular sieve of the present invention is used as the catalyst, and the reaction of cyclohexanone, ammonia and hydrogen peroxide is performed at 1 atm and 40 to 110° C., preferably 50 to 90° C., to form cyclohexanone oxime. The mole ratio of ammonia to cyclohexanone is in a range from 1.2:1 to 2:1, preferably 1.4:1 to 1.8:1; and the mole ratio of hydrogen peroxide to cyclohexanone is in a range from 0.7:1 to 2.0:1, preferably 1.0:1 to 1.5:1. The solvent may be a polar solvent such as an alcohol, a ketone or water. Preferably, the solvent may be tert-butanol. The amount of the catalyst may be 0.1 to 10%, and preferably 1 to 5%, of the total amount of the reactants.

In addition, the concentration of hydrogen peroxide may be 30 wt % to 70 wt %, and the hydrogen peroxide may be gradually added into the reaction system.

Comparative Example 1

In this embodiment, no transition metal source is used for preparing the titanium-silicalite molecular sieve.

A flask (500 ml) was nitrogen sealed under vacuum. 1.98 g of tetrabutyl titanate was added into the flask, and then cooled down to 5° C. Then, 20 g of anhydrous isopropanol was added and stirred. Upon temperature equilibrium, 30 g of tetraethyl silicate was dropped into the flask, and then stirred for 1 hour. 56 g (20 wt %) of tetrapropylammonium hydroxide solution was dropped into the flask, and then stirred. Then, the mixture was heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiments 1-13 provided various preparations of titanium-silicalite molecular sieves having various metal oxides.

Embodiment 1

V-TS-1 Preparation (Catalyst A)

A flask (500 ml) was nitrogen sealed under vacuum. 1.932 g of tetrabutyl titanate was added into the flask, and then cooled down to 5° C. Upon temperature equilibrium, 30.27 g of tetraethyl silicate was dropped into the flask, and then stirred for 1 hour. 56.5 g (20 wt %) of tetrapropylammonium hydroxide isopropanol solution was dropped into the flask. 0.19 g of vanadyl sulfate hydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 2

Fe-TS-1 Preparation (Catalyst B)

A flask (500 ml) was nitrogen sealed under vacuum. 1.98 g of tetrabutyl titanate was added into the flask, and then cooled down to 5° C. Upon temperature equilibrium, 30 g of tetraethyl silicate was dropped into the flask, and then stirred for 1 hour. 56 g (20 wt %) of tetrapropylammonium hydroxide isopropanol solution was dropped into the flask. 0.39 g of ferric chloride hexahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst. The X-ray spectrum of this catalyst was shown in FIG. 1. All the catalysts prepared from Embodiments of the present invention had the MFI structure.

Embodiment 3

Co-TS-1 Preparation (Catalyst C)

A flask (500 ml) was nitrogen sealed under vacuum. 1.98 g of tetrabutyl titanate was added into the flask, and then cooled down to 5° C. Upon temperature equilibrium, 30 g of tetraethyl silicate was dropped into the flask, and then stirred for 1 hour. 56 g (20 wt %) of tetrapropylammonium hydroxide isopropanol solution was dropped into the flask. 0.0143 g of cobaltous acetate tetrahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 4

Ni-TS-1 Preparation (Catalyst D)

A flask (500 ml) was nitrogen sealed under vacuum. 1.99 g of tetrabutyl titanate was added into the flask, and then cooled down to 5° C. Upon temperature equilibrium, 30.6 g of tetraethyl silicate was dropped into the flask, and then stirred for 1 hour. 57 g (20 wt %) of tetrapropylammonium hydroxide isopropanol solution was dropped into the flask. 0.0012 g of nickel chloride hexahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 5

Zn-TS-1 Preparation (Catalyst E)

A flask (500 ml) was nitrogen sealed under vacuum. 1.98 g of tetrabutyl titanate was added into the flask, and then cooled down to 5° C. Upon temperature equilibrium, 30 g of tetraethyl silicate was dropped into the flask, and then stirred for 1 hour. 56 g (20 wt %) of tetrapropylammonium hydroxide isopropanol solution was dropped into the flask. 0.17 g of zinc nitrate hexahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 6

Zr-TS-1 (Catalyst F)

A flask (500 ml) was nitrogen sealed under vacuum. 1.98 g of tetrabutyl titanate was added into the flask, and then cooled down to 5° C. Upon temperature equilibrium, 30.54 g of tetraethyl silicate was dropped into the flask, and then stirred for 1 hour. 57 g (20 wt %) of tetrapropylammonium hydroxide isopropanol solution was dropped into the flask. 0.024 g of zirconium sulfate tetrahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 7

Ru-TS-1 Preparation (Catalyst G)

A flask (500 ml) was nitrogen sealed under vacuum. 1.98 g of tetrabutyl titanate was added into the flask, and then cooled down to 5° C. Upon temperature equilibrium, 30.14 g of tetraethyl silicate was dropped into the flask, and then stirred for 1 hour. 56 g (20 wt %) of tetrapropylammonium hydroxide isopropanol solution was dropped into the flask. 0.016 g of ruthenium chloride hydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 8

Pd-TS-1 Preparation (Catalyst H)

A flask (500 ml) was nitrogen sealed under vacuum. 1.94 g of tetrabutyl titanate was added into the flask, and then cooled down to 5° C. Upon temperature equilibrium, 30.34 g of tetraethyl silicate was dropped into the flask, and then stirred for 1 hour. 56 g (20 wt %) of tetrapropylammonium hydroxide isopropanol solution was dropped into the flask. 0.102 g of palladium chloride was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 9

Y-TS-1 Preparation (Catalyst I)

A flask (500 ml) was nitrogen sealed under vacuum. 1.98 g of tetrabutyl titanate was added into the flask, and then cooled down to 5° C. Upon temperature equilibrium, 30.05 g of tetraethyl silicate was dropped into the flask, and then stirred for 1 hour. 56 g (20 wt %) of tetrapropylammonium hydroxide isopropanol solution was dropped into the flask. 0.153 g of yttrium acetate tetrahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 10

Hf-TS-1 Preparation (Catalyst J)

A flask (500 ml) was nitrogen sealed under vacuum. 1.97 g of tetrabutyl titanate was added into the flask, and then cooled down to 5° C. Upon temperature equilibrium, 30.13 g of tetraethyl silicate was dropped into the flask, and then stirred for 1 hour. 56 g (20 wt %) of tetrapropylammonium hydroxide isopropanol solution was dropped into the flask. 0.154 g of hafnium sulfate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 11

Cr-TS-1 Preparation (Catalyst K)

A flask (500 ml) was nitrogen sealed under vacuum. 1.97 g of tetrabutyl titanate was added into the flask, and then cooled down to 5° C. Upon temperature equilibrium, 30.11 g of tetraethyl silicate was dropped into the flask, and then stirred for 1 hour. 56 g (20 wt %) of tetrapropylammonium hydroxide isopropanol solution was dropped into the flask. 0.002 g of chromium nitrate nonahydrate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 12

Mn-TS-1 Preparation (Catalyst L)

A flask (500 ml) was nitrogen sealed under vacuum. 1.98 g of tetrabutyl titanate was added into the flask, and then cooled down to 5° C. Upon temperature equilibrium, 30.4 g of tetraethyl silicate was dropped into the flask, and then stirred for 1 hour. 57 g (20 wt %) of tetrapropylammonium hydroxide isopropanol solution was dropped into the flask. 0.001 g of manganese sulfate was dissolved in 20 ml of water, and then this solution was dropped into the flask. Then, the mixture was stirred, then heated at 85° C. to remove alcohol, and added with water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 550° C. for 8 hours, so as to obtain the catalyst.

Embodiment 13

Fe-TS-1 Preparation with Addition of Colloidal Silica (Catalyst M)

A flask (500 ml) was nitrogen sealed under vacuum. 1.98 g of tetrabutyl titanate was added into the flask, and then cooled down to 5° C. Upon temperature equilibrium, 30 g of tetraethyl silicate was dropped into the flask, and then stirred for 1 hour. 56 g (20 wt %) of tetrapropylammonium hydroxide isopropanol solution was dropped into the flask. 0.23 g of ferric chloride hexahydrate was dissolved in 20 ml of water, and then this solution was dropped into the flask. Then, the mixture was stirred, then heated at 85° C. to remove alcohol, and added with 10.80 g of Ludox AS-40 and water to form total weight of 100 g, so as to obtain the gel mixture. The gel mixture was sealed in a stainless steel can, and was heated at 180° C. for 120 hours. Then, the solid was separated from the liquid, and was cleaned with pure water to be neutral. The solid was dried at 100° C., and calcined at 500° C. for 8 hours, so as to obtain the catalyst.

Embodiment 14

The titanium-silicalite molecular sieves prepared from Comparative Example 1 and Embodiments 1-8 were respectively used as the catalyst for the preparation of cyclohexanone oxime.

0.55 g of the catalyst was placed in a flask, and added with 5 g of cyclohexanone, 28.5 g of tert-butanol and 4.7 g (28 wt %) of ammonia. The reaction system was equipped with a condensation tube and a stirring device. The temperature of the reaction system was heated to 60° C., and then 4.96 g of 35 wt % hydrogen peroxide solution (ketone:$H_2O_2$=1.0:1.0) was gradually added in 5 hours to perform the preparation of cyclohexanone oxime. Upon 1 hour after the introduction of hydrogen peroxide, the catalyst was separated from the reaction solution. Then, the reaction solution was analyzed. The results were shown in Table 1.

TABLE 1

| Molecular sieve catalyst | $X^a$ | $S^b$ | $X^c$ | $S^d$ |
|---|---|---|---|---|
| Comparative Example (TS-1) | 95.27% | 96.49% | 99.25% | 92.58% |
| Catalyst A | 96.22% | 97.46% | 99.31% | 94.38% |
| Catalyst B | 97.82% | 99.50% | 99.81% | 97.37% |
| Catalyst C | 96.60% | 98.39% | 99.69% | 95.20% |
| Catalyst D | 96.00% | 97.78% | 99.25% | 94.50% |
| Catalyst E | 96.35% | 96.76% | 99.40% | 93.57% |
| Catalyst F | 95.65% | 98.83% | 99.39% | 95.11% |
| Catalyst G | 96.57% | 97.86% | 99.56% | 95.37% |
| Catalyst H | 96.20% | 98.36% | 99.72% | 94.81% |

$X^a$ = conversion rate of cyclohexanone = moles of consumed cyclohexanone/initial moles of cyclohexanone × 100%
$S^b$ = selectivity of cyclohexanone oxime = moles of produced cyclohexanone oxime/moles of consumed cyclohexanone × 100%
$X^c$ = conversion rate of hydrogen peroxide = moles of consumed hydrogen peroxide/initial moles of hydrogen peroxide × 100%
$S^d$ = selectivity of hydrogen peroxide = moles of produced cyclohexanone oxime/moles of consumed hydrogen peroxide × 100%

Embodiment 15

The titanium-silicalite molecular sieves prepared from Comparative Example 1, Embodiment 2 and Embodiments 9-12 were respectively used as the catalyst for the preparation of cyclohexanone oxime.

0.55 g of the catalyst was placed in a flask, and added with 5 g of cyclohexanone, 28.5 g of tert-butanol and 4.7 g (28 wt %) of ammonia. The reaction system was equipped with a condensation tube and a stirring device. The temperature of the reaction system was heated to 60° C., and then 5.20 g of 35 wt % hydrogen peroxide solution (ketone:$H_2O_2$=1.00:1.05) was gradually added in 5 hours to perform the preparation of cyclohexanone oxime. Upon 1 hour after the introduction of hydrogen peroxide, the catalyst was separated from the reaction solution. Then, the reaction solution was analyzed. The results were shown in Table 2.

TABLE 2

| Molecular sieve catalyst | $X^a$ | $S^b$ | $X^c$ | $S^d$ |
|---|---|---|---|---|
| Comparative Example (TS-1) | 99.17% | 98.03% | 99.52% | 92.95% |
| Catalyst B | 99.23% | 99.39% | 99.40% | 94.92% |
| Catalyst I | 99.35% | 98.58% | 99.29% | 94.02% |
| Catalyst J | 99.24% | 98.58% | 99.13% | 93.99% |
| Catalyst K | 99.74% | 98.89% | 99.09% | 94.80% |
| Catalyst L | 99.29% | 98.67% | 99.56% | 93.59% |

Embodiment 16

The titanium-silicalite molecular sieves prepared from Comparative Example 1, Embodiments 1, 2, 3, 5 and 13 were respectively used as the catalyst for the preparation of cyclohexanone oxime.

0.55 g of the catalyst was placed in a flask, and added with 5 g of cyclohexanone, 28.5 g of tert-butanol and 4.7 g (28 wt %) of ammonia. The reaction system was equipped with a condensation tube and a stirring device. The temperature of the reaction system was heated to 60° C., and then 5.35 g of 35 wt % hydrogen peroxide solution (ketone:$H_2O_2$=1.00:1.08) was gradually added in 5 hours to perform the preparation of cyclohexanone oxime. Upon 1 hour after the introduction of hydrogen peroxide, the catalyst was separated from the reaction solution. Then, the reaction solution was analyzed. The results were shown in Table 3.

TABLE 3

| Molecular sieve catalyst | $X^a$ | $S^b$ | $X^c$ | $S^d$ |
|---|---|---|---|---|
| Comparative Example (TS-1) | 99.22% | 98.02% | 99.31% | 90.58% |
| Catalyst A | 99.09% | 99.30% | 98.60% | 93.09% |
| Catalyst B | 99.33% | 99.59% | 99.51% | 92.70% |
| Catalyst C | 99.70% | 99.33% | 99.33% | 92.26% |
| Catalyst E | 99.88% | 98.08% | 99.03% | 92.10% |
| Catalyst M | 99.96% | 99.55% | 99.34% | 92.91% |

Accordingly, in the method of the present invention, the transition metal source is mixed with the titanium source, silicon source and the template agent before the gem mixture is formed, such that the titanium-silicalite molecular sieve of the present invention has the transition metal oxide. The method for preparing cyclohexanone oxime by using the titanium-silicalite molecular sieve of the present invention results in high conversion rate, high selectivity, and high usage efficiency of hydrogen peroxide.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing a titanium-silicalite molecular sieve, comprising the steps of:
   preparing a mixture of a titanium source, a silicon source, a transition metal source, a template agent and water, wherein the template agent is dissolved in an alcohol solvent;
   heating the mixture to form a gel mixture;
   heating the gel mixture in a water bath; and
   calcining the gel mixture after the gel mixture in the water bath to form the titanium-silicalite molecular sieve.

2. The method of claim 1, wherein the titanium source is tetraalkyl titanate.

3. The method of claim 1, wherein the silicon source is tetraalkyl silicate or polyethoxysiloxane.

4. The method of claim 1, wherein the template agent is tetrapropylammonium hydroxide.

5. The method of claim 1, wherein the template agent is dissolved in the alcohol solvent in a concentration of 5 wt % to 50 wt %, and the gel mixture mixed with the water is heated to remove the solvent.

6. The method of claim 5, wherein the alcohol solvent is one or more selected from the group consisting of methanol, ethanol, isopropanol, n-butanol and tert-butanol.

7. The method of claim 1, wherein a mole ratio of the template agent to the silicon source is less than or equal to 0.5.

8. The method of claim 1, wherein the transition metal source is selected from the group consisting of an acidic metal salt, a metal alkoxide and a metal complex.

9. The method of claim 8, the transition metal source is dissolved in the water and mixed in an aqueous form with the titanium source, the silicon source and the template agent to form the gel mixture.

10. The method of claim 1, wherein the transition metal source is dissolved in the water including ammonia.

11. The method of claim 1, wherein a molar ratio of titanium to silicon in the titanium-silicalite molecular sieve ranges from 0.005 to 0.1, and a molar ratio of the transition metal to the silicon in the titanium-silicalite molecular sieve ranges from 0.00001 to 0.05.

12. The method of claim 1, further comprising the steps of:
   after forming the gel mixture, mixing the gel mixture with water or colloidal silica; and
   heating the gel mixture mixed with the water or the colloidal silica in the water bath.

13. The method of claim 12, wherein the colloidal silica is silicon dioxide gel solution, and an amount of the silicon dioxide is 0.1 to 50 wt % of the silicon dioxide gel solution.

14. The method of claim 12, wherein a weight ratio of the colloidal silica to the gel mixture ranges from 0.001:1 to 0.5:1.

* * * * *